US012569457B2

(12) United States Patent
Jiang et al.

(10) Patent No.: US 12,569,457 B2
(45) Date of Patent: Mar. 10, 2026

(54) COATED BETA HYDROXYBUTYRIC ACID CRYSTAL AND METHODS FOR PRODUCING THE SAME

(71) Applicant: NANJING NUTRABUILDING BIO-TECH CO., LTD., Nanjing (CN)

(72) Inventors: Long Jiang, Nanjing (CN); Yang Zhu, Nanjing (CN); Ronghua Yi, Nanjing (CN); Kylin Liao, Nanjing (CN); Qiru Fan, Nanjing (CN)

(73) Assignee: NANJING NUTRABUILDING BIO-TECH CO., LTD., Nanjing (CN)

( * ) Notice: Subject to any disclaimer, the term of this patent is extended or adjusted under 35 U.S.C. 154(b) by 290 days.

(21) Appl. No.: 18/486,572

(22) Filed: Oct. 13, 2023

(65) Prior Publication Data

US 2024/0033235 A1 Feb. 1, 2024

Related U.S. Application Data

(63) Continuation of application No. PCT/CN2022/086731, filed on Apr. 14, 2022.

(30) Foreign Application Priority Data

Apr. 16, 2021 (WO) ................ PCT/CN2021/087824

(51) Int. Cl.
| | |
|---|---|
| *A61K 31/19* | (2006.01) |
| *A61K 9/16* | (2006.01) |
| *A61K 9/50* | (2006.01) |

(52) U.S. Cl.
CPC ............ *A61K 31/19* (2013.01); *A61K 9/1652* (2013.01); *A61K 9/1694* (2013.01); *A61K 9/501* (2013.01); *A61K 9/5015* (2013.01); *A61K 9/5042* (2013.01)

(58) Field of Classification Search
CPC ...................................................... A61K 31/19
See application file for complete search history.

(56) References Cited

U.S. PATENT DOCUMENTS 8,529,954 B2 * 9/2013 Lebon .................. A61K 9/5047
424/490

FOREIGN PATENT DOCUMENTS

| | | | |
|---|---|---|---|
| CA | 2902911 A1 | | 4/2016 |
| CN | 102215822 A | * | 10/2011 |
| CN | 103347503 A | | 10/2013 |
| CN | 109806251 A | | 5/2019 |
| CN | 111511355 A | | 8/2020 |

OTHER PUBLICATIONS

World Intellectual Property Organization (WIPO) International Search Report for PCT/CN2022/086731 Jul. 26, 2022 6 pages.

* cited by examiner

*Primary Examiner* — Carlos A Azpuru
(74) *Attorney, Agent, or Firm* — ANOVA LAW GROUP, PLLC

(57) ABSTRACT

Coated beta-hydroxybutyrate (BHB) free acid crystal pellets/granules are provided, which comprise BHB free acid crystal, fillers, and coating material. Methods for producing coated BHB free acid crystal pellets/granules are provided, which may include (a) wet granulation, (b) extrusion, (c) spheronization, and (d) coating, such as coating material spray embedding through Wurster bottom spray coating device.

19 Claims, No Drawings

COATED BETA HYDROXYBUTYRIC ACID CRYSTAL AND METHODS FOR PRODUCING THE SAME

CROSS-REFERENCE TO RELATED APPLICATION

This Application is a continuation application of International Patent Application No. PCT/CN2022/086731, filed on Apr. 14, 2022, which claims the benefit of the International Patent Application PCT/CN2021/087824, filed on Apr. 16, 2021, the disclosures of all of which are incorporated herein by reference in their entirety.

BACKGROUND

Nutritional, or therapeutic, ketosis is the physiological state of elevated blood ketone body levels resulting from ketogenic diets, calorie restriction, therapeutic fasting, and/or supplementation with ketogenic precursors. When in ketosis, the body is essentially burning fat for its primary fuel, and begins cleaving fats into fatty acids and glycerol and transforms the fatty acids into acetyl CoA molecules, which are then eventually transformed through ketogenesis into ketone bodies beta-hydroxybutyrate (beta-hydroxybutyrate or "BHB"), acetoacetate (acetylacetonate), and acetone in the liver. BHB and acetoacetate are the ketone bodies used by the body for energy while acetone is removed as a by-product of ketogenesis. Ketone bodies represent alternative energy substrates for both peripheral tissues and the central nervous system.

While Beta-hydroxybutyrate (BHB) salts have been used as supplementary ketone source for years, they may result in the excess intake of metal ions. In order to reduce the intake of excessive metal cations, BHB free acid may be a better choice. Nevertheless, BHB free acid crystals are easily deliquescent crystals, which are prone to deliquesce in the air and become a solution state, and thus cannot maintain their crystal morphology. This becomes a major problem in their storage and application, and thus blocks the potential commercialization of BHB acid. In addition, even in the crystal state, BHB free acid still undergoes a self-polymerization reaction due to the influences of external environmental during storage, forming dimers, trimers, and multimer compounds, and loses its value for use.

To overcome these drawbacks, it is therefore desired to have an improved form of BHB free acid products, and production methods thereof, with desired form and uniform particle size, to effectively improve the stability of the BHB free acid crystals and prevent self-polymerization.

SUMMARY

This summary is provided to introduce a selection of concepts in a simplified form that is further described below in the Detailed Description. This summary is not intended to identify key features or essential features of the claimed subject matter, nor is it intended to be used to limit the scope of the claimed subject matter.

The present disclosure generally relates to formulations of coated (e.g., film-coated) beta-hydroxybutyrate (BHB) free acid crystal pellets/granules (pellets and/or granules), and methods for producing such coated BHB free acid crystal pellets/granules. Particularly, the BHB free acid crystals may be granulated, shot blasted and coated, and the surface of the BHB free acid pellets/granules is successfully coated with uniform film through Wurster coating, and the coated granules effectively prevent the BHB free acid crystals from deliquescing. Since such BHB free acid crystals are isolated from the external environment and avoid absorption of environmental moisture, the coated BHB free acid crystal pellets/granules according to the present disclosure are able to prevent self-polymerization of the BHB free acid crystals and have substantially improved stability.

One aspect of the present disclosure relates to a coated beta-hydroxybutyrate (BHB) free acid crystal pellet/granule, comprising a BHB free acid crystal, a filler, and a coating material.

In some embodiments, the coated BHB free acid crystal pellet(s)/granule(s) are made of raw materials comprising (a) the BHB free acid crystal with a mass percentage ranging from 10.00% to 99.00%; (b) the filler with a mass percentage ranging from 1.00% to 60.00%; and (c) the coating material with a mass percentage ranging from 0.10% to 80.00%.

In some further embodiments, the coated BHB free acid crystal pellet(s)/granule(s) are made of raw materials comprising (a) the BHB free acid crystal with a mass percentage ranging from 50.00% to 95.00%; (b) the filler with a mass percentage ranging from 1.00% to 30.00%; and (c) the coating material with a mass percentage ranging from 1.00% to 45.00%.

In some embodiments, the BHB free acid crystal comprises D-BHB, DL-BHB, and L-BHB forms or a mixture thereof (e.g., a mixture of any two or any three thereof, in any ratio).

In some embodiments, the filler comprises microcrystalline cellulose, lactose, mannitol, starch, sodium starch octenyl succinate, pregelatinized starch, sodium carboxymethyl cellulose, sodium carboxymethyl starch, cross-linked sodium carboxymethyl starch, resistant dextrin, methyl cellulose, hydroxypropyl methyl cellulose, hydroxyethyl cellulose, $\beta$-cyclodextrin, or a mixture thereof (e.g., a mixture of any two or any three thereof, in any ratio).

In some embodiments, the coating material comprises hydroxypropyl methyl cellulose, carrageenan, xanthan gum, gum arabic, modified starch, polyvinyl alcohol, titanium dioxide, talc, triacetin, pigments, or a mixture thereof (e.g., a mixture of any two or any three thereof, in any ratio).

Still, in some embodiments, the coated BHB free acid crystal pellet/granule has a particle size ranging from 10 to 80 mesh.

Another aspect of the present disclosure provides a composition for promoting and/or sustaining ketosis in a mammal (e.g., human or animal), comprising coated BHB free acid crystal pellet(s)/graules(s) as described above.

In a further aspect, the prevent disclosure relates to a method for preparing the coated BHB free acid crystal pellets/granules. The preparation method may include (a) wet granulation, (b) extrusion, (c) spheronization, and (d) coating (e.g., coating material spray embedding through Wurster bottom spray coating device).

In some embodiments, the wet granulation step comprises: mixing a BHB free acid crystal and a filler; and adding a binder solution (e.g., water) to obtain a wet material.

In some further embodiments, the mixing ratio of the BHB free acid crystal and the filler ranges from 99:1 to 40:60 (weight by weight or volume by volume); and/or the ratio of the filler and binder solution ranges from 1:1 to 1:1.5 (weight by weight or volume by volume).

Still, in some further embodiments, the stirring motor rotating speed of wet granulator is 10~200 rounds/minute ("r/min"), speed of the shearing head is 50~600 r/min, and/or feeding speed is 5-15 r/min.

In some embodiments, the extrusion step comprises extruding the wet material obtained in step (a) by an extruder, to obtain a strip material with the same diameter. For instance, the extruder may have sieve plate aperture of 0.3-0.8 mm, and/or the screw speed of the extruder may be 100-300 r/min.

In some embodiments, the spheronization step comprises: sphering the strip materials obtained in step (b) at a high speed through a spheronization device to obtain pellets/granules with the same size and desired roundness.

In some further embodiments, the rotation speed of the spheronization device is 400-1500 r/min, and/or the time of spheronization may be 15 s-10 min.

In some embodiments, the drying step comprising: drying the pellets/granules prepared in step (c) to obtain BHB free acid crystal pellets/granules. In some embodiments, the moisture content of final material is controlled below 5%. In some further embodiments, the drying temperature may be 20-50° C.; and/or the drying time may be 15-30 min.

In some embodiments, the coating step comprising: coating the BHB free acid crystal pellets/granules prepared in step (d) with a coating material by a Wurster coater. In some embodiments, the air inlet speed of the Wurster coater may be 15-30 Hz, the coating temperature may be 20-50° C., feeding speed of coating liquid is 1-20 r/min, and/or the coating weight may gain 0.1%-80%. Drying for 15-25 min after completed coating, the moisture content of final material may be controlled less than 3.0%.

In some embodiments, the coated BHB free acid crystal pellets/granules have a uniform particle size.

In some embodiments, the coated BHB free acid crystal pellets/granules have a particle size ranging from 10 to 80 mesh.

In some embodiments, the BHB free acid crystal comprises D-BHB, DL-BHB, and L-BHB forms or a mixture thereof.

In some embodiments, the filler comprises microcrystalline cellulose, lactose, mannitol, starch, sodium starch octenyl succinate, pregelatinized starch, sodium carboxymethyl cellulose, sodium carboxymethyl starch, cross-linked sodium carboxymethyl starch, resistant dextrin, methyl cellulose, hydroxypropyl methyl cellulose, hydroxyethyl cellulose, β-cyclodextrin, or a mixture thereof.

In some embodiments, the coating material comprises hydroxypropyl methyl cellulose, carrageenan, xanthan gum, gum arabic, modified starch, polyvinyl alcohol, titanium dioxide, talc, triacetin, pigments, or a mixture thereof.

In some embodiments, the effective content of BHB free acid in the prepared coated BHB free acid crystal pellets/granules are adjustable, up to 99.00%.

Still in some embodiments, the method effectively prevents BHB acid crystals from absorbing environmental moisture, prevents self-polymerization, improves storage stability, prevents the deliquescent problem of BHB free acid and prolongs the shelf life; improves the fluidity of BHB acid and facility to process and package; increases the intake of BHB in oral unit dose; avoids the intake of metal ions; and/or covers up the sour taste of BHB acid crystals.

As used herein, the term "granule" means a particle that has been coated by the liquid product and then solidified/dried and shaped in the fluidized bed of the granulator to form solid particles with at least a core and an outer layer of the coating.

As used herein, the term "pellet" refers to a small unit of material compressed into any of several shapes and sizes, e.g., cylindrical, rectangular, or spherical. Pellets may also include additional agents to help bind the material compressed into the pellet.

As used herein, the term "or" is meant to include both "and" and "or." In other words, the term "or" may also be replaced with "and/or."

Unless otherwise specifically indicated, the technical and scientific terms used in the framework of the present disclosure have generally accepted meanings known to those skilled in the art to which the present disclosure relates. In the text of the description and claims, the singular also includes plural references, unless the context clearly dictates otherwise. For example, the term "granule" may include many granules. As used herein, the singular forms "a," "an" and "the" are intended to include the plural forms as well, unless the context clearly indicates otherwise.

DETAILED DESCRIPTION

Reference will now be made in detail to the preferred embodiments of the present disclosure, examples of which are further illustrated. While the present disclosure will be described in conjunction with the preferred embodiments, it will be understood that they are not intended to limit the present disclosure to these embodiments. To the contrary, the present disclosure is intended to cover alternatives, modifications and equivalents, which may be included within the spirit and scope of the present disclosure as defined by the claims. Furthermore, in the detailed description of the present disclosure, numerous specific details are set forth in order to provide a thorough understanding of the present disclosure. However, it will be obvious to one of ordinary skill in the art that the present disclosure may be practiced without these specific details. In other instances, well known methods, procedures, components, and other features have not been described in detail as not to unnecessarily obscure aspects of the present disclosure.

Generally speaking, various embodiments of the present disclosure provide for formulations of coated BHB free acid crystal pellets/granules, which include BHB free acid crystal, fillers, and coating material, as well as methods for producing coated BHB free acid crystal pellets/granules. Specifically, the production methods of BHB salt pellets/granules according to the present disclosure may include (a) wet granulation, (b) extrusion, (c) spheronization, and (d) coating (e.g., coating material spray embedding through Wurster bottom spray coating device).

The present disclosure may achieve a number of technical advantages. First, the coated BHB free acid crystal pellets/granules according to the present disclosure have a uniform particle size (e.g., 10-80 mesh) and uniform coating film. Accordingly, compared with conventional BHB free acid crystal, the coated BHB free acid crystal pellets/granules according to the present disclosure achieved significantly improved fluidity, and thus are much easier to be used for downstream product manufacturing. Second, the effective content of BHB free acid in the prepared coated granules is adjustable (e.g., up to 99.00%). Third, the coated BHB free acid crystal pellets/granules according to the present disclosure can effectively prevent the deliquescent problem of BHB free acid and prolong the shelf life, so that BHB free acid crystals can be used directly in dietary supplements. Fourth, the coated BHB free acid crystal pellets/granules according to the present disclosure are able to prevent the self-polymerization of BHB free acid during storage due to their coating. Fifth, compared with BHB salts, taking coated beta hydroxybutyric acid (BHB) can avoid the intake of metal cations such as $Na^+$, $Ka^+$, $Mg^{2+}$, $Ca^{2+}$. Sixth, because of the limitation of manufacture process and raw materials, trace amounts of lead are inevitable in BHB calcium salt. Compared with BHB calcium salt, taking coated Beta hydroxybutyric acid (BHB) can avoid the intake of heavy metal cations such as $Pb^{2+}$. Last but not least, the coated Beta hydroxybutyric acid (BHB) can cover up the sour taste of BHB free acid crystal.

The following examples are illustrative of select embodiments of the present disclosure and are not meant to limit the scope of the present disclosure.

EXAMPLE 1

The formulation of BHB free acid crystal pellets/granules in Example 1 is made of the raw materials with the respective mass percentages, as shown in Table 1 below.

TABLE 1

| Component name | Mass (kg) | Mass percentage (%) |
|---|---|---|
| BHB free acid crystal | 3.00 | 92.31 |
| Microcrystalline cellulose | 0.05 | 1.54 |
| Sodium starch octenyl succinate | 0.05 | 1.54 |
| Coating material | 0.15 | 4.62 |

The preparation method of such coated BHB free acid crystal pellets/granules include the following steps:

(1) Wet granulation: Mix 3 kg of BHB free acid crystals, 0.05 kg of microcrystalline cellulose and 0.05 kg of sodium starch octenyl succinate, add 0.12 kg of water for wet granulation to obtain wet materials. The stirring motor rotating speed of the wet granulator is adjusted to 45 r/min, the speed of the shearing head is 400 r/min and the feeding speed of the binder is 6 r/min;

(2) Extrusion: Extrude the wet material obtained in step (1) by the extruder with the sieve plate aperture of 0.6 mm, to obtain strip materials with the same diameter. The screw speed of the extruder is adjusted to 150 r/min;

(3) Spheronization: Sphere the strip materials obtained in step (2) at the high speed through the spheronization device to get pellets/granules of the same size and good roundness. The rotation speed of the spheronization device is adjusted to 760 r/min and the time of spheronization is 30 s;

(4) Drying: Dry the pellets/granules prepared in step (3) to get BHB free acid crystal pellets/granules. The drying temperature is adjusted to 45° C. and the drying time is 25 min;

(5) Coating: Coating the BHB free acid crystal pellets/granules prepared in step (4) by Wurster coater with coating material, which is dissolved in water or ethanol at a solid content of 20% for use. The air inlet speed of the Wurster coater is 22 Hz and the coating temperature is 45° C., and the feeding speed of the coating liquid is 10 r/min. Drying for 15 min after coating is completed to obtain the coated BHB free acid crystal.

The coated BHB free acid crystal pellets/granules were subjected to a controlled temperature of 25° C./60% RH. The products were subjected to stability testing at the following time intervals: 0 time, 3 months, 6 months, 9 months, and 12 months. The results of the stability test are set forth in Table 2 below.

TABLE 2

| Time Periods at 25° C./60% RH | Stability of Coated BHB Free Acid | | Stability of BHB Free Acid Crystal | |
|---|---|---|---|---|
| | Moisture Content (%) | Dipolymer Content (%) | Moisture Content (%) | Dipolymer Content (%) |
| 0 time | 0.28 | 0.3 | 0.50 | 0.38 |
| 3 months | 0.63 | 0.31 | 2.14 | 1.42 |
| 6 months | 1.26 | 0.63 | 10.63 | 4.29 |
| 9 months | 1.71 | 1.18 | 18.16 | 10.65 |
| 12 months | 2.39 | 1.67 | 29.97 | 29.07 |

EXAMPLE 2

The formulation of BHB free acid crystal pellets/granules in Example 2 is made of the raw materials with the respective mass percentages, as shown in Table 3 below.

TABLE 3

| Component name | Mass (kg) | Mass percentage (%) |
|---|---|---|
| BHB free acid crystal | 3.00 | 95.24 |
| Microcrystalline cellulose | 0.05 | 1.59 |
| Coating material | 0.10 | 3.17 |

The preparation method of such coated BHB free acid crystal pellets/granules includes the following steps:

(1) Wet granulation: Mix 3 kg of BHB free acid crystals and 0.05 kg of microcrystalline fiber, add 0.06 kg of water for wet granulation to obtain wet materials. The stirring motor rotating speed of the wet granulator is adjusted to 45 r/min, the speed of the shearing head is 800 r/min and the feeding speed of the binder is 5 r/min;

(2) Extrusion: Extrude the wet material obtained in step (1) by the extruder with the sieve plate aperture of 0.8 mm, to obtain strip materials with the same diameter. The screw speed of the extruder is adjusted to 150 r/min. The wet material obtained in step (1) is extruded in an extruder with a 0.8 mm aperture through a sieve plate, and the rotation speed of the extruder is adjusted to 150 r/min. Obtain strip materials with the same diameter;

(3) Spheronization: Sphere the strip materials obtained in step (2) at the high speed through the spheronization device to get pellets/granules of the same size and good roundness. The rotation speed of the spheronization device is adjusted to 1000 r/min and the time of spheronization is 6 min;

(4) Drying: Dry the pellets/granules prepared in step (3) to get BHB free acid crystal pellets/granules. The drying temperature is adjusted to 35° C. and the drying time is 25 min;

(5) Coating: Coating the BHB free acid crystal pellets/granules prepared in step (4) by Wurster coater with coating material, which is dissolved in water or ethanol at a solid content of 20% for use. The air inlet speed of the Wurster coater is 25 Hz and the coating temperature is 38° C., and the feeding speed of the coating liquid is 2 r/min. Drying for 15 min after coating is completed to obtain the coated BHB free acid crystal.The coated BHB free acid crystal pellets/granules were subjected to a controlled temperature of 25° C./60% RH. The products were subjected to stability testing at the following time intervals: 0 time, 3 months, 6 months, 9 months, and 12 months. The results of the stability test are set forth in Table 4 below.

TABLE 4

| Time Periods at 25° C./60% RH | Stability of Coated BHB Free Acid | | Stability of BHB Free Acid Crystal | |
| | Moisture Content (%) | Dipolymer Content (%) | Moisture Content (%) | Dipolymer Content (%) |
| --- | --- | --- | --- | --- |
| 0 time | 0.3 | 0.31 | 0.50 | 0.38 |
| 3 months | 1.93 | 1.15 | 2.14 | 1.42 |
| 6 months | 8.26 | 6.83 | 10.63 | 4.29 |
| 9 months | 13.57 | 9.98 | 18.16 | 10.65 |
| 12 months | 21.39 | 17.24 | 29.97 | 29.07 |

EXAMPLE 3

The formulation of BHB free acid crystal pellets/granules in Example 3 is made of the raw materials with the respective mass percentages, as shown in Table 5 below.

TABLE 5

| Component name | Mass (kg) | Mass percentage (%) |
| --- | --- | --- |
| BHB free acid crystal | 3.00 | 96.77 |
| Hydroxypropyl methylcellulose | 0.02 | 0.65 |
| Coating material | 0.08 | 2.58 |

The preparation method of such coated BHB free acid crystal pellets/granules includes the following steps:

(1) Wet granulation: Mix 3 kg of BHB free acid crystals and 0.02 kg of hydroxypropyl methylcellulose, add 0.05 kg of water for wet granulation to obtain wet materials. The stirring motor rotating speed of the wet granulator is adjusted to 50 r/min, the speed of the shearing head is 100 r/min and the feeding speed of the binder is 6 r/min;

(2) Extrusion: Extrude the wet material obtained in step (1) by the extruder with the sieve plate aperture of 0.8 mm, to obtain strip materials with the same diameter. The screw speed of the extruder is adjusted to 100 r/min;

(3) Spheronization: Sphere the strip materials obtained in step (2) at the high speed through the spheronization device to get pellets/granules of the same size and good roundness. The rotation speed of the spheronization device is adjusted to 1100 r/min and the time of spheronization is 7 min;

(4) Drying: Dry the pellets/granules prepared in step (3) to get BHB free acid crystal pellets/granules. The drying temperature is adjusted to 45° C. and the drying time is 25 min;

(5) Coating: Coating the BHB free acid crystal pellets/granules prepared in step (4) by Wurster coater with coating material, which is dissolved in water or ethanol at a solid content of 20% for use. The air inlet speed of the Wurster coater is 23 Hz and the coating temperature is 45° C., and the feeding speed of the coating liquid is 4 r/min. Drying for 15 min after coating is completed to obtain the coated BHB free acid crystal.

The coated BHB free acid crystal pellets/granules were subjected to a controlled temperature of 25° C./60% RH. The products were subjected to stability testing at the following time intervals: 0 time, 3 months, 6 months, 9 months, and 12 months. The results of the stability test are set forth in Table 6 below.

TABLE 6

| Time Periods at 25° C./60% RH | Stability of Coated BHB Free Acid | | Stability of BHB Free Acid Crystal | |
| | Moisture Content (%) | Dipolymer Content (%) | Moisture Content (%) | Dipolymer Content (%) |
| --- | --- | --- | --- | --- |
| 0 time | 0.3 | 0.32 | 0.50 | 0.38 |
| 3 months | 1.52 | 0.54 | 2.14 | 1.42 |
| 6 months | 9.16 | 4.20 | 10.63 | 4.29 |
| 9 months | 16.93 | 10.24 | 18.16 | 10.65 |
| 12 months | 26.34 | 28.03 | 29.97 | 29.07 |

EXAMPLE 4

The formulation of BHB free acid crystal pellets/granules in Example 4 is made of the raw materials with the respective mass percentages, as shown in Table 7 below.

TABLE 7

| Component name | Mass (kg) | Mass percentage (%) |
| --- | --- | --- |
| BHB free acid crystal | 3.00 | 90.91 |
| Hydroxypropyl methylcellulose | 0.02 | 0.61 |
| Resistant dextrin | 0.2 | 6.06 |
| Coating material | 0.08 | 2.44 |

The preparation method of such coated BHB free acid crystal pellets/granules includes the following steps:

(1) Wet granulation: Mix 3 kg of BHB free acid crystals, 0.02kg of hydroxypropyl methylcellulose and 0.2kg of resistant dextrin, add 0.25 kg of water for wet granulation to obtain wet materials. The stirring motor rotating speed of the wet granulator is adjusted to 50 r/min, the speed of the shearing head is 100 r/min and the feeding speed of the binder is 6 r/min;

(2) Extrusion: Extrude the wet material obtained in step (1) by the extruder with the sieve plate aperture of 0.8 mm, to obtain strip materials with the same diameter. The screw speed of the extruder is adjusted to 145 r/min;

(3) Spheronization: Sphere the strip materials obtained in step (2) at the high speed through the spheronization device to get pellets/granules of the same size and good roundness. The rotation speed of the spheronization device is adjusted to 800 r/min and the time of spheronization is 11 min;

(4) Drying: Dry the pellets/granules prepared in step (3) to get BHB free acid crystal pellets/granules. The drying temperature is adjusted to 45° C. and the drying time is 25 min;

(5) Coating: Coating the BHB free acid crystal pellets/granules prepared in step (4) by Wurster coater with coating material, which is dissolved in water or ethanol at a solid content of 20% for use. The air inlet speed of the Wurster coater is 23 Hz and the coating temperature is 45° C., and the feeding speed of the coating liquid is 4 r/min. Drying for 15 min after coating is completed to obtain the coated BHB free acid crystal.

The coated BHB free acid crystal pellets/granules were subjected to a controlled temperature of 25° C./60% RH. The products were subjected to stability testing at the following time intervals: 0 time, 3 months, 6 months, 9 months, and 12 months. The results of the stability test are set forth in Table 8 below.

TABLE 8

| Time Periods at 25° C./60% RH | Stability of Coated BHB Free Acid | | Stability of BHB Free Acid Crystal | |
| | Moisture Content (%) | Dipolymer Content (%) | Moisture Content (%) | Dipolymer Content (%) |
| --- | --- | --- | --- | --- |
| 0 time | 0.15 | 0.18 | 0.50 | 0.38 |
| 3 months | 0.31 | 0.34 | 2.14 | 1.42 |
| 6 months | 0.49 | 0.58 | 10.63 | 4.29 |
| 9 months | 0.73 | 0.86 | 18.16 | 10.65 |
| 12 months | 0.99 | 1.07 | 29.97 | 29.07 |

EXAMPLE 5

The formulation of BHB free acid crystal pellets/granules in Example 5 is made of the raw materials with the respective mass percentages, as shown in Table 9 below.

TABLE 9

| Component name | Mass (kg) | Mass percentage (%) |
| --- | --- | --- |
| BHB free acid crystal | 3.00 | 90.91 |
| Hydroxypropyl methylcellulose | 0.02 | 0.61 |
| β-cyclodextrin | 0.2 | 6.06 |
| Coating material | 0.08 | 2.44 |

The preparation method of such coated BHB free acid crystal pellets/granules includes the following steps:

(1) Wet granulation: Mix 3 kg of BHB free acid crystals, 0.02 kg of hydroxypropyl methylcellulose and 0.2 kg of β-cyclodextrin, add 0.25 kg of water for wet granulation to obtain wet materials. The stirring motor rotating speed of the wet granulator is adjusted to 50 r/min, the speed of the shearing head is 100 r/min and the feeding speed of the binder is 6 r/min;

(2) Extrusion: Extrude the wet material obtained in step (1) by the extruder with the sieve plate aperture of 0.8 mm, to obtain strip materials with the same diameter. The screw speed of the extruder is adjusted to 145 r/min;

(3) Spheronization: Sphere the strip materials obtained in step (2) at the high speed through the spheronization device to get pellets/granules of the same size and good roundness. The rotation speed of the spheronization device is adjusted to 800 r/min and the time of spheronization is 11 min;

(4) Drying: Dry the pellets/granules prepared in step (3) to get BHB free acid crystal pellets/granules. The drying temperature is adjusted to 45° C. and the drying time is 25 min;

(5) Coating: Coating the BHB free acid crystal pellets/granules prepared in step (4) by Wurster coater with coating material, which is dissolved in water or ethanol at a solid content of 20% for use. The air inlet speed of the Wurster coater is 23 Hz and the coating temperature is 45° C., and the feeding speed of the coating liquid is 4 r/min. Drying for 15 min after coating is completed to obtain the coated BHB free acid crystal.

The coated BHB free acid crystal pellets/granules were subjected to a controlled temperature of 25° C./60% RH. The products were subjected to stability testing at the following time intervals: 0 time, 3 months, 6 months, 9 months, and 12 months. The results of the stability test are set forth in Table 10 below.

TABLE 10

| Time Periods at 25° C./60% RH | Stability of Coated BHB Free Acid | | Stability of BHB Free Acid Crystal | |
| | Moisture Content (%) | Dipolymer Content (%) | Moisture Content (%) | Dipolymer Content (%) |
| --- | --- | --- | --- | --- |
| 0 time | 0.15 | 0.18 | 0.50 | 0.38 |
| 3 months | 0.18 | 0.21 | 2.14 | 1.42 |
| 6 months | 0.23 | 0.24 | 10.63 | 4.29 |
| 9 months | 0.27 | 0.29 | 18.16 | 10.65 |
| 12 months | 0.32 | 0.35 | 29.97 | 29.07 |

EXAMPLE 6

The formulation of BHB free acid crystal pellets/granules in Example 6 is made of the raw materials with the respective mass percentages, as shown in Table 11 below.

TABLE 11

| Component name | Mass (kg) | Mass percentage (%) |
| --- | --- | --- |
| BHB free acid crystal | 3.00 | 90.91 |
| Sodium starch octenyl succinate | 0.02 | 0.61 |
| β-cyclodextrin | 0.2 | 6.06 |
| Coating material | 0.08 | 2.44 |

The preparation method of such coated BHB free acid crystal pellets/granules includes the following steps:

(1) Wet granulation: Mix 3 kg of BHB free acid crystals, 0.02 kg of starch sodium octenyl succinate and 0.2 kg of β-cyclodextrin, add 0.25 kg of water for wet granulation to obtain wet materials. The stirring motor rotating speed of the wet granulator is adjusted to 50 r/min, the speed of the shearing head is 120 r/min and the feeding speed of the binder is 6 r/min;

(2) Extrusion: Extrude the wet material obtained in step (1) by the extruder with the sieve plate aperture of 0.6 mm, to obtain strip materials with the same diameter. The screw speed of the extruder is adjusted to 145 r/min;

(3) Spheronization: Sphere the strip materials obtained in step (2) at the high speed through the spheronization device to get pellets/granules of the same size and good roundness. The rotation speed of the spheronization device is adjusted to 1200 r/min and the time of spheronization is 6 min;

(4) Drying: Dry the pellets/granules prepared in step (3) to get BHB free acid crystal pellets/granules. The drying temperature is adjusted to 45° C. and the drying time is 25 min;

(5) Coating: Coating the BHB free acid crystal pellets/granules prepared in step (4) by Wurster coater with coating material, which is dissolved in water or ethanol at a solid content of 20% for use. The air inlet speed of the Wurster coater is 26 Hz and the coating temperature is 45° C., and the feeding speed of the coating liquid is 4 r/min. Drying for 15 min after coating is completed to obtain the coated BHB free acid crystal.

The coated BHB free acid crystal pellets/granules were subjected to a controlled temperature of 25° C./60% RH. The products were subjected to stability testing at the following time intervals: 0 time, 3 months, 6 months, 9 months, and 12 months. The results of the stability test are set forth in Table 12 below.

TABLE 12

| Time Periods at 25° C./60% RH | Stability of Coated BHB Free Acid | | Stability of BHB Free Acid Crystal | |
|---|---|---|---|---|
| | Moisture Content (%) | Dipolymer Content (%) | Moisture Content (%) | Dipolymer Content (%) |
| 0 time | 0.15 | 0.18 | 0.50 | 0.38 |
| 3 months | 0.23 | 0.26 | 2.14 | 1.42 |
| 6 months | 0.26 | 0.31 | 10.63 | 4.29 |
| 9 months | 0.32 | 0.39 | 18.16 | 10.65 |
| 12 months | 0.64 | 0.65 | 29.97 | 29.07 |

EXAMPLE 7

The formulation of BHB free acid crystal pellets/granules in Example 7 is made of the raw materials with the respective mass percentages, as shown in Table 13 below.

TABLE 13

| Component name | Mass (kg) | Mass percentage (%) |
|---|---|---|
| BHB free acid crystal | 3.00 | 92.31 |
| Microcrystalline cellulose | 0.05 | 1.54 |
| Lactose | 0.05 | 1.54 |
| Coating material | 0.15 | 4.62 |

The preparation method of such coated BHB free acid crystal pellets/granules includes the following steps:

(1) Wet granulation: Mix 3 kg of BHB free acid crystals, 0.05 kg of microcrystalline cellulose and 0.05 kg of lactose, add 0.12 kg of water for wet granulation to obtain wet materials. The stirring motor rotating speed of the wet granulator is adjusted to 45 r/min, the speed of the shearing head is 400 r/min and the feeding speed of the binder is 6 r/min;

(2) Extrusion: Extrude the wet material obtained in step (1) by the extruder with the sieve plate aperture of 0.6 mm, to obtain strip materials with the same diameter. The screw speed of the extruder is adjusted to 150 r/min;

(3) Spheronization: Sphere the strip materials obtained in step (2) at the high speed through the spheronization device to get pellets/granules of the same size and good roundness. The rotation speed of the spheronization device is adjusted to 760 r/min and the time of spheronization is 30 s;

(4) Drying: Dry the pellets/granules prepared in step (3) to get BHB free acid crystal pellets/granules. The drying temperature is adjusted to 45° C. and the drying time is 25 min;

(5) Coating: Coating the BHB free acid crystal pellets/granules prepared in step (4) by Wurster coater with coating material, which is dissolved in water or ethanol at a solid content of 20% for use. The air inlet speed of the Wurster coater is 22 Hz and the coating temperature is 45° C., and the feeding speed of the coating liquid is 10 r/min. Drying for 15 min after coating is completed to obtain the coated BHB free acid crystal.

The coated BHB free acid crystal pellets/granules were subjected to a controlled temperature of 25° C./60% RH. The products were subjected to stability testing at the following time intervals: 0 time, 3 months, 6 months, 9 months, and 12 months. The results of the stability test are set forth in Table 14.

TABLE 14

| Time Periods at 25° C./60% RH | Stability of Coated BHB Free Acid | | Stability of BHB Free Acid Crystal | |
|---|---|---|---|---|
| | Moisture Content (%) | Dipolymer Content (%) | Moisture Content (%) | Dipolymer Content (%) |
| 0 time | 0.28 | 0.3 | 0.50 | 0.38 |
| 3 months | 1.53 | 0.45 | 2.14 | 1.42 |
| 6 months | 3.17 | 1.84 | 10.63 | 4.29 |
| 9 months | 6.32 | 2.36 | 18.16 | 10.65 |
| 12 months | 9.54 | 5.75 | 29.97 | 29.07 |

Although specific embodiments and examples of the present disclosure have been illustrated herein, it will be appreciated by those skilled in the art that any modifications and variations can be made without departing from the spirit of the present disclosure. The examples and illustrations above are not intended to limit the scope of the present disclosure. Any combination of embodiments of the present disclosure, along with any obvious their extension or analogs, are within the scope of the present disclosure. Further, it is intended that the present disclosure encompass any arrangement, which is calculated to achieve that same purpose, and all such variations and modifications as fall within the scope of the appended claims.

All the features disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example of a generic series of equivalent or similar features.

Other Embodiments

It is to be understood that while the present disclosure has been described in conjunction with the detailed description thereof and accompanying figures, the foregoing description and accompanying figures are only intended to illustrate, and not limit the scope of the present disclosure, which is defined by the scope of the appended claims. Other aspects, advantages, and modifications are within the scope of the following claims. All publications referenced herein are incorporated by reference in their entireties.

What is claimed is:

1. A coated beta-hydroxybutyrate (BHB) free acid crystal pellet/granule, comprising a BHB free acid crystal, a filler, and a coating material, wherein the coated BHB free acid crystal pellets/granules are made of raw materials comprising (a) the BHB free acid crystal with a mass percentage ranging from 10.00% to 99.00%; (b) the filler with a mass percentage ranging from 1.00% to 60.00%; and (c) the coating material with a mass percentage ranging from 0.10% to 80.00%.

2. The coated BHB free acid crystal pellet/granule of claim 1, wherein the coated BHB free acid crystal pellets/granules are made of raw materials comprising (a) the BHB free acid crystal with a mass percentage ranging from 50.00% to 95.00%; (b) the filler with a mass percentage ranging from 1.00% to 30.00%; and (c) the coating material with a mass percentage ranging from 1.00% to 45.00%.

3. The coated BHB free acid crystal pellet/granule of claim 1, wherein the BHB free acid crystal comprises D-BHB, DL-BHB, and L-BHB forms or a mixture thereof.

4. The coated BHB free acid crystal pellet/granule of claim 1, wherein the filler comprises microcrystalline cellulose, lactose, mannitol, starch, sodium starch octenyl succinate, pregelatinized starch, sodium carboxymethyl cellulose, sodium carboxymethyl starch, cross-linked sodium carboxymethyl starch, resistant dextrin, methyl cellulose, hydroxypropyl methyl cellulose, hydroxyethyl cellulose, β-cyclodextrin, or a mixture thereof.

5. The coated BHB free acid crystal pellet/granule of claim 1, wherein the coating material comprises hydroxypropyl methyl cellulose, carrageenan, xanthan gum, gum arabic, modified starch, polyvinyl alcohol, titanium dioxide, talc, triacetin, pigments, or a mixture thereof.

6. The coated BHB free acid crystal pellet/granule of claim 1, wherein the coated BHB free acid crystal pellet/granule has a particle size ranging from 10 to 80 mesh.

7. A composition for promoting and/or sustaining ketosis in a mammal, comprising a coated BHB free acid crystal pellet/granule of claim 1.

8. A method for preparing coated BHB free acid crystal pellets/granules, comprising (a) wet granulation, (b) extrusion, (c) spheronization, and (d) coating, wherein the wet granulation step comprises: mixing a BHB free acid crystal and a filler;
and adding a binder solution to obtain a wet material.

9. The method of claim 8, wherein the coating step comprises coating material spray embedding through Wurster bottom spray coating device.

10. The method of claim 8, wherein the mixing ratio of the BHB free acid crystal and the filler ranges from 99:1 to 40:60 (weight by weight or volume by volume); and/or the ratio of the filler and binder solution ranges from 1:1 to 1:1.5 (weight by weight or volume by volume).

11. The method of claim 8, wherein the extrusion step comprises extruding the wet material obtained in step (a) by an extruder, to obtain a strip material with the same diameter.

12. The method of claim 8, wherein the spheronization step comprises:
sphering the strip materials obtained in step (b) at a high speed through a spheronization device to obtain pellets/granules with the same size and desired roundness.

13. The method of claim 8, wherein the drying step comprising: drying the pellets/granules prepared in step (c) to obtain BHB free acid crystal pellets/granules.

14. The method of claim 13, wherein moisture content of final material is controlled below 5%.

15. The method of claim 8, wherein the coating step comprising: coating the BHB free acid crystal pellets/granules prepared in step (d) with a coating material by a Wurster coater.

16. The method of claim 15, wherein the coated BHB free acid crystal pellets/granules have a particle size ranging from 10 to 80 mesh.

17. The method of claim 8, wherein the filler comprises microcrystalline cellulose, lactose, mannitol, starch, sodium starch octenyl succinate, pregelatinized starch, sodium carboxymethyl cellulose, sodium carboxymethyl starch, cross-linked sodium carboxymethyl starch, resistant dextrin, methyl cellulose, hydroxypropyl methyl cellulose, hydroxyethyl cellulose, B-cyclodextrin, or a mixture thereof.

18. The method of claim 15, wherein the coating material comprises hydroxypropyl methyl cellulose, carrageenan, xanthan gum, gum arabic, modified starch, polyvinyl alcohol, titanium dioxide, talc, triacetin, pigments, or a mixture thereof.

19. A method for preparing coated BHB free acid crystal pellets/granules, comprising (a) wet granulation, (b) extrusion, (c) spheronization, and (d) coating, wherein the wet granulation step comprises: mixing a BHB free acid crystal and a filler; and adding a binder solution to obtain a wet material, wherein the mixing ratio of the BHB free acid crystal and the filler ranges from 99:1 to 40:60 (weight by weight or volume by volume).

* * * * *